United States Patent [19]

Truett

[11] Patent Number: 5,728,301

[45] Date of Patent: Mar. 17, 1998

[54] APPARATUS AND METHOD FOR THIN LAYER CHROMATOGRAPHY

[76] Inventor: William L. Truett, Stone Farm Unit 321, 42 Wolf Dr., Lebanon, N.H. 03766-1953

[21] Appl. No.: 638,337

[22] Filed: Apr. 26, 1996

Related U.S. Application Data

[63] Continuation-in-part of Ser. No. 314,707, Sep. 29, 1994, abandoned.

[51] Int. Cl.$^6$ ................................................. B01D 15/08
[52] U.S. Cl. ........................ 210/635; 210/658; 210/198.3
[58] Field of Search ........................... 210/635, 656, 210/658, 198.2, 198.3; 422/69; 436/162

[56] References Cited

U.S. PATENT DOCUMENTS

| | | | |
|---|---|---|---|
| 3,455,818 | 7/1969 | Leifield | 210/658 |
| 3,553,067 | 1/1971 | Dwyer | 210/198.3 |
| 3,591,805 | 7/1971 | Schoeffel | 210/198.3 |
| 3,757,490 | 9/1973 | Ma | 210/198.3 |
| 3,915,856 | 10/1975 | Meyer | 210/198.3 |
| 3,963,421 | 6/1976 | Jones | 210/658 |
| 4,272,380 | 6/1981 | Jones | 210/658 |
| 4,443,339 | 4/1984 | Rosevear | 210/658 |
| 4,512,896 | 4/1985 | Gershoni | 210/198.3 |
| 4,671,870 | 6/1987 | Tompa | 210/198.3 |
| 4,671,871 | 6/1987 | Szekely | 210/198.3 |
| 4,678,570 | 7/1987 | Meszaros | 210/658 |
| 4,743,373 | 5/1988 | Rai | 210/198.3 |
| 4,863,610 | 9/1989 | Campbell | 210/198.3 |
| 5,147,539 | 9/1992 | Hagen | 210/198.3 |
| 5,340,746 | 8/1994 | Hagen | 210/198.3 |

FOREIGN PATENT DOCUMENTS

WO 9301494  1/1993  WIPO ........................... 210/658

*Primary Examiner*—Ernest G. Therkorn
*Attorney, Agent, or Firm*—Herbert M. Wolfson

[57] ABSTRACT

A method for spectral analysis of mixtures is disclosed using thin layer chromatography for separation of the components of the mixture followed by taking FTIR spectroscopic readings along the vertical length of the coated support.

2 Claims, 1 Drawing Sheet

5,728,301

APPARATUS AND METHOD FOR THIN LAYER CHROMATOGRAPHY

CROSS REFERENCE TO RELATED APPLICATION

This application is a continuation-in-part of U.S. patent application Ser. No. 08/314,707, filed Sep. 29, 1994, now abandoned.

FIELD OF THE INVENTION

This invention relates to the use of thin layer chromatography (TLC) to analyze chemical mixtures.

BACKGROUND OF THE INVENTION

In conventional thin layer chromatography, a glass plate, or a sheet of aluminum or plastic is used as the carrier of a sorption layer of silica or alumina. After placing a spot of the mixture to be analyzed on the plate, the plate is placed in contact with an appropriate solvent which ascends the sorption layer on the plate due to capillary action. This causes the spot representing the mixture to be separated into the components in the mixture in accordance with the solubility of the component in the ascending solvent. Thus, each separated spot represents one of the compounds that make up the mixture. Each spot must then be removed from the plate along with its sorption carrier layer in order to be analyzed. There is at present no simple method to accomplish this removal. Typically, the sorption layers with the separated spots are scraped from the plate and the chemical (s) eluted from the sorption material. Only after this procedure is completed can the structure of the chemicals be determined.

Furthermore, there is no TLC apparatus which can be used in a spectral analysis procedure which does not first require similar scraping and eluting, as described above, before the spectral analysis can be performed.

Accordingly, it is an object of the present invention to provide a TLC apparatus and a simplified method of TLC analysis, wherein the TLC separations are performed and the spectral analysis is accomplished without requiring scraping and/or eluting of the sorption layers.

Other objects will appear hereinafter.

SUMMARY OF THE INVENTION

The invention comprises a method of analysis by infrared spectroscopy using thin layer chromatography (TLC) to separate a mixture into its components. The device for performing TLC comprises a support, e.g. screen, scrim, membrane, grid, mesh (of metal, glass fibers, etc.), preferably a support in the form of a screen, that is substantially opaque to infrared radiation, upon which is deposited a thin layer of any of the known chromatographic sorption materials, e.g. alumina, silica, cellulose, polymeric materials (polyamide, etc.).

Specifically, the method invention comprises the following steps:

(a) forming a slurry by mixing at least one chromatographic material selected from the group consisting of alumina, keisilguhr, attapulgite clay, silica gel, cellulose and polyamide in a suitable inert liquid;

(b) depositing a thin layer of the slurry on a support that is unaffected by the solvent and that is substantially opaque to infrared radiation;

(c) drying the slurry on the support to form a support coated with the dried slurry;

(d) dissolving a mixture of organic compounds to be analyzed in a solvent for the mixture to form a solution;

(e) placing the coated support formed in step (c) vertically in the solution formed in step (a) so that the bottom edge of the coated support is in the solution;

(f) waiting a sufficient time for the solution to rise by capillary action, preferably to the top edge of the support; and then, optionally drying the coated support before (g) exposing the resulting coated support to infra-red energy at a plurality of positions along the vertical length of the support to provide a plurality of infrared spectra at various levels from the bottom to the top of the support, each of the vertically disposed infrared spectrum representing one of the organic compounds that had been dissolved in the solvent to form the solution in step (d).

Thus, this invention provides a relatively simple method to analyze the components of a chemical mixture after the components have been separated into individual components via thin layer chromatography. In summary, the chromatographic sorption material, such as alumina, is first placed on a screen matrix. The mixture to be analyzed is then "applied" to the coated screen by "developing", i.e. rising via capillary action after being placed in a solvent for such "development". After the separation has occurred, the screen is dried, preferably, rather than merely allowed to dry. The dried screen strip or plate is then placed in the FTIR (Fourier Transform Infra-Red) spectrometer and the spectrum determined at about every 8–10 mm of the height of the plate, starting from the point where the sample mixture was first applied to the screen support. In this fashion, a series of spectra are obtained. For example, if the mixture contained benzoic acid, salicylic acid and biphenyl, the IR spectra of those chemicals would be "read" in that order along the vertical height of the plate.

DETAILED DESCRIPTION OF THE PREFERRED EMBODIMENT

Figure 1:
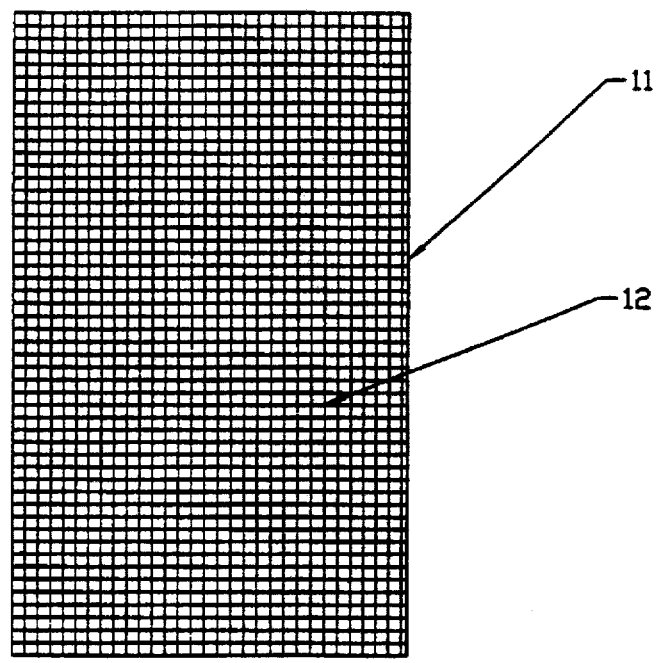
FIG. 1 is a simplified front view illustration and FIG. 2 is a side view illustration of the apparatus used in the present invention.
Figure 2:
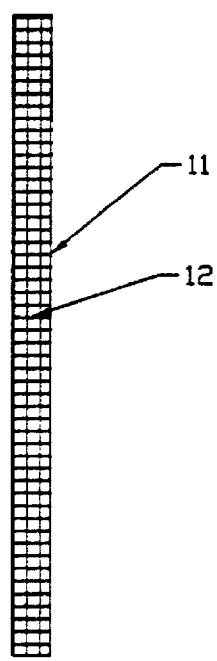

The preferred device, as shown in FIG. 1, consists of a screen matrix 11 covered with chromatographic sorption material 12 that is prepared as follows:

First, a slurry of aluminum oxide in toluene is prepared by stirring these materials rapidly to form a suspension. Two –three mls of the suspension are then placed on the screen matrix and allowed to dry. The slurry should be spread onto the screen as thinly as possible and the slurry should be nearly transparent when dry. Drying the coated screen usually requires 15–30 minutes at room temperature.

A mixture of organic components is prepared by dissolving 100 mg of benzophenone and 100 mg of benzoic acid in 2 mls of toluene. One drop of this mixture is placed ¼ inch from the bottom edge of the coated screen. Next, the screen containing the drop of mixture to be analyzed is placed in a beaker containing 1/16 inch of toluene. Capillary action then draws the toluene upward to cover the screen and to cause separation of the components of the mixture being analyzed. The screen may be removed from the beaker when the toluene reaches the top of the screen. The screen containing the separated components is next allowed to dry.

To perform an analysis of the separated components, the screen is placed in an FTIR spectrometer so that the bottom ⅓ of the screen is in the path of the beam of infrared energy. The spectrum of this section of the screen is recorded; the spectrum will be that of benzoic acid. The screen is repositioned to place the top ⅓ of the screen in the path of the beam of infrared energy. Recording a spectrum from this area reveals that of benzophenone.

This method is unique in that the TLC separation and the FTIR analysis of the components of the mixture can be performed on the same device. The screen may be used to analyze any substances for which TLC is normally employed.

The preferred screen has a mesh of about 1-2 millimeter openings, but may range anywhere from as little as an 0.1 millimeter opening to openings of 10 millimeters. The size of the openings must be such that adequate energy is transmitted through the chromatographic coating on the screen to provide a readable IR spectrum. It is recognized that the FTIR spectrometer usually requires passage of from 5 to 40% energy through the screen in order to realize a usable spectrum.

The screen material can comprise any plastic, metal, or glass fiber. The only practical requirement is that the screen not be attacked by the solvents or reagents used in the chromatographic process. In actual practice, stainless steel or fiber glass screens have been found to be most satisfactory.

The thickness of the sorption layer of chromatographic material placed on the screen may be anywhere from 0.01 to about 1.0 millimeter, preferably about 0.1 to 1.0 millimeter.

It is important for easy determination of the spectra of the materials to be analyzed that the screen material used is opaque to infrared radiation. Membrane cells, which are usually composed of either polyethylene or polytetrafluoroethylene membranes, materials which are not opaque to IR radiation, may also be used. However, the spectra of these polymetic materials must be factored into the spectral readings obtained before concluding the analysis.

It is also important that the IR absorbance of the chromatographic material be reliably low. The most transparent of these materials is silica gel. However, aluminum oxide, when applied to a thickness no greater than 1.0 millimeter, is equally useful.

In the earlier description, the separation and analysis of a mixture of benzophenone and benzoic acid in toluene are described using aluminum oxide as the chromatographic material. Another separation and analysis (spectral determination) was performed using a mixture of benzoic acid, salicylic acid and biphenyl in a small volume of toluene. 0.01 milliliter of this mixture was applied to a screen that had been coated with a layer of alumina no more than 1.0 millimeter thick. The coated screen was "developed" using acetone as the solvent. After the screen is fully "developed" by capillary action, the screen is dried and then examined via FTIR spectroscopy. First, the area of the original spot was examined. A spectrum was then determined at intervals of 8 millimeters above the spot. Three spectra were obtained in this manner. The first being identical to that of benzoic acid, the second being that of salicylic acid and the third being that of biphenyl.

What is claimed is:

1. A method for analyzing a mixture of compounds that are soluble in a single solvent comprising:

(a) forming a slurry by mixing at least one chromatographic material selected from the group consisting of alumina, silica, keisilguhr, attapulgite clay, cellulose and polyamide in a suitable, inert liquid;

(b) depositing a thin layer of said slurry on a support selected from the group consisting of a screen, scrim, membrane, grid and a mesh of metal or glass fiber that is unaffected by said inert liquid and that is substantially opaque to infrared radiation;

(c) drying said slurry on said support to form a support coated with a layer about 0.01 to about 1.6 millimeters thick of said slurry;

(d) dissolving a mixture of organic compounds in a solvent for said mixture to form a solution;

(e) placing said coated support vertically in said solution so that only the bottom edge of said coated support is within said solution;

(f) allowing sufficient time for said solution to rise by capillary action to a reasonable vertical distance of said coated support; and (g) exposing the resulting coated support to infra-red energy along the height of said support to provide a plurality of infra-red spectra at various levels from the bottom to the top of said support, each spectrum representing each of the organic compounds dissolved in the solvent in step (d).

2. The method of claim 1 wherein said chromatographic composition used in step (a) is alumina in toluene and said support is a screen.

* * * * *